USOO5633153A

United States Patent [19]
Ursin

[11] Patent Number: 5,633,153
[45] Date of Patent: May 27, 1997

[54] ALDEHYDE DEHYDROGENASE SELECTABLE MARKERS FOR PLANT TRANSFORMATION

[75] Inventor: Virginia M. Ursin, Davis, Calif.

[73] Assignee: Calgene, Inc., Davis, Calif.

[21] Appl. No.: 324,130

[22] Filed: Oct. 14, 1994

[51] Int. Cl.$^6$ .......................... C12N 15/00; C12N 5/04; C12N 15/82; A01H 5/00
[52] U.S. Cl. ...................... 435/172.3; 435/69.1
[58] Field of Search ........................ 435/172.3, 69.1, 435/240.4, 183, 240.49; 800/205

[56] References Cited

PUBLICATIONS

Li et al (1992) Plant Physiol 100:662–668.
Boyd, et al., "Characterization of an *Escherichia Coli* Gene Encoding Betaine Aldehyde Dehydrogenase (BADH) Structural Similarity to Mammalian ALDHs and a Plant BADH", *Gene* (1991), 103 45–52.
Holmstrom, et al., "Production of the *Escherichia coli* Betaine–Aldehyde Dehydrogenase, an Enzyme Required for the Synthesis of the Osmoprotectant Glycine Betaine, in Transgenic Plants" *The Plant Journal* (1994) 6(5) 749–758.
McCue, et al "Salt–Inducible Betaine, Aldehyde Dehydrogenase from Sugar Beet: cDNA Cloning and Expression" *Plant Molecular Biology* (1992) 18 1–11.
Rathinasabapathi, et al., "Matabolic Engineering of Glycine Betaine Synthesis: Plant Betaine Aldehyde Dehydrogenases Lacking Typical Transit Peptides are Targeted to Tobacco Chloroplasts where they Confer Betaine Aldehyde Resistance" *Planta* (1994) 193 155–162.
Weretilnyk, et al., "Molecular Cloning of a Plant Betaine–Aldehyde Dehydrogenase, an Enzyme Implicated in Adaptation to Salinity and Drought" *Proc. Nat. Acad. Sci.* (1990) vol. 87 2745–2749.

*Primary Examiner*—David T. Fox
*Assistant Examiner*—Elizabeth F. McElwain
*Attorney, Agent, or Firm*—Bell, Seltzer, Park & Gibson; W. Murray Spruill

[57] ABSTRACT

The instant application provides a method of plant transformation in which plant cells are transformed with an aldehyde dehydrogenase gene capable of detoxifying a phytotoxic aldehyde selective agent. Transformed plant cells are cultured in the presence of the phytotoxic aldehyde selective agent to produce transformed shoots which may be regenerated to produce transformed plant cells containing the aldehyde dehydrogenase gene. The aldehyde dehydrogenase gene construct is linked to another gene construct of interest for expression in plant cells, wherein the aldehyde dehydrogenase gene acts as a selectable marker for transgenic plant cells containing the desired gene construct.

21 Claims, No Drawings

ALDEHYDE DEHYDROGENASE SELECTABLE MARKERS FOR PLANT TRANSFORMATION

Technical Field

The present invention is directed to a method of plant transformation in which toxic aldehydes are used as the selective agent in conjunction with an aldehyde dehydrogenase which acts to detoxify the aldehyde compound.

INTRODUCTION

Background

Methods of producing stably transformed plants through "genetic engineering" have been developed over the past decade. These genetic engineering techniques have resulted in numerous genetic modifications to various plant species, including such crop plants as tomato, cotton, Brassica, corn and soybeans. Generally, the methods used in obtaining transformed plants, including DNA bombardment, Agrobacterium-mediated transformation, protoplast fusion and microinjection, rely on the use of a marker gene construct. The marker gene construct is inserted into the plant genome, along with the construct for a desired phenotypic modification. Expression of the marker construct is relied upon to select cells which have been stably transformed. Often, the selectable marker gene is of bacterial origin and confers antibiotic resistance upon transformed plant cells. This resistance characteristic allows for selection of the transformed cells in a growth medium which contains levels of the antibiotic sufficient to prohibit or greatly reduce growth of non-transformed plant cells.

Although such antibiotic resistance marker gene constructs are useful in generating transformed plants, it is desirable to develop additional selectable marker systems to provide options for plant transformation, for example for a second transformation of a transgenic plant where a second marker is required, and to provide selection systems which do not rely on antibiotic resistance for selection.

Relevant Literature

Cloning of a spinach gene encoding betaine aldehyde dehydrogenase was reported by Weretilnyk et al. (*Proc. Nat. Acad. Sci.* (1990) 87:2745–2749).

Cloning of a gene encoding betaine aldehyde dehydrogenase from sugar beet was reported by McCue et al. (*Plant Mol. Biol.* (1992) 18:1–11.

Cloning of a gene encoding betaine aldehyde dehydrogenase from *E. coli* was reported by Boyd et al. (*Gene* (1991) 103:45–52.

Transformation of tobacco with plant betaine aldehyde dehydrogenase genes was reported by Rathinasabapathi et al. (*Planta* (1994) 193:155–162).

SUMMARY OF THE INVENTION

The instant invention is directed to selectable marker systems useful in plant transformation. A method of selecting transformed plant cells is provided in which a DNA construct for expression of a gene encoding an aldehyde dehydrogenase enzyme is introduced into plant cells, wherein the plant cells are sensitive to growth inhibition by an aldehyde substrate of the aldehyde dehydrogenase enzyme. The plant cells are then cultured in a plant growth medium which comprises an inhibitory concentration of the aldehyde substrate. In this manner, transformed plant cells containing the construct for expression of an aldehyde dehydrogenase enzyme may be selected by the ability to grow in the presence of the toxic aldehyde compound.

The aldehyde substrates of the aldehyde dehydrogenase enzymes used in the instant invention are small aldehyde compounds, such as acetaldehyde, formaldehyde, proprionaldehyde, butyraldehyde, or betaine aldehyde, which are toxic to plant cells of many plant species. Of particular interest, is the use of a betaine aldehyde dehydrogenase enzyme in a method of transforming various crop plant species, including tomato and tobacco, using betaine aldehyde as the selective agent.

DETAILED DESCRIPTION OF THE INVENTION

The plant transformation method of the instant invention involves the use of phytotoxic aldehyde compounds capable of inhibiting the growth of plant cells in culture as a selective agent, and provides as a marker which can be used to select for transformed plant cells, an aldehyde dehydrogenase (ALDH) gene capable of detoxifying the aldehyde selective agent.

The phytotoxic aldehyde compounds considered in the instant invention are small aldehydes, such as acetaldehyde, formaldehyde, proprionaldehyde, butyraldehyde, or betaine aldehyde. Phytotoxicity of a particular aldehyde compound to a target plant species may be assessed by conducting a "kill curve" to demonstrate adverse growth or developmental effects to plant cells, and to determine appropriate levels of the phytotoxic aldehyde to be included in cell culture media for selection against cells sensitive to growth inhibition by the aldehyde compound.

The aldehyde dehydrogenase selectable marker will consist of a gene construct for expression of an aldehyde dehydrogenase in plant cells. The ALDH encoding region of the constructs may be obtained from a variety of sources, so long as the gene, when expressed in plant cells, is capable of providing resistance to the aldehyde selective agent such that transformed plant cells containing the ALDH gene may be selected and further grown to produce transgenic plants. For example aldehyde dehydrogenase genes have been cloned from diverse organisms, such as mammals, fungi, yeast, bacteria and plants. A description of various clones ALDH genes is found in Boyd et al. (*Gene* (1991) 103:45–52).

Aldehyde dehydrogenases are a large family of enzymes that catalyze the oxidation of aldehydes to carboxylic acids. Most exhibit a broad, but unique, substrate specificity. For example, human ALDH1 and ALDH2 play a major role in detoxification of acetaldehyde in the liver, while ALDH3 utilizes benzaldehyde and heptaldehyde as optimal substrates. ALDH3 may play a major role in the detoxification of toxic stomach aldehydes. ALDH4 is most active for glutamic-gamma-semialdehyde (Hsu, et al. (1992) *J. Biol. Chem.* 267:3030–3037.

For the most part, the ALDH structural gene will be from a natural source, although in some situations it may be desirable to modify all or a portion of the codons, for example to enhance expression, by employing host-preferred codons. The gene may be synthesized in whole or in part, particularly where it is desirable to provide plant preferred codons, such as when the ALDH gene is from a non-plant source. Plant preferred codons may be determined from the codons of highest frequency in the proteins expressed in the largest amount in the particular plant species of interest. Methods for synthesizing sequences and bringing the sequences together are well established in the literature. In vitro mutagenesis and selection, site-directed mutagenesis, or other means may be employed to obtain mutations of a naturally occurring ALDH gene to produce an enzyme with more desirable physical and kinetic parameters for function in the plant cell, such as a higher affinity for the substrate aldehyde.

A method to obtain an ALDH with a substrate specificity for a specific phytotoxic aldehyde would involve culturing on media containing the particular aldehyde, *E. coli* strains deficient in ALDH activity carrying and expressing specific ALDH genes, or random cDNAs of plant, fungal, mammalian or bacterial origin. Complementation of the deficiency in the *E. coli* strain would permit the strains to grow in the presence of the selecting aldehyde. The sequences confirming the best complementation can be used in the preparation of a plant expression cassette for introduction into plants.

The aldehyde dehydrogenase construct will contain gene regulatory regions to provide for expression of the ALDH gene encoding sequence in plant cells. A promoter region from a gene expressed in plant cells is provided 5' to the ALDH encoding sequence to provide for transcription in plant cells. Promoters which provide for expression in plant cells in culture are required in order to impart resistance to the selective agent. Such promoter regions are known in the art, and are obtainable, for example from native plant genes, for example the ribulose bisphosphate carboxylase small subunit transcriptional initiation region. Alternatively, promoters from plant viral genes, such as the cauliflower mosaic virus CaMV 35S promoter, or those associated with T-DNA such as the opine synthase transcriptional initiation regions, for example, octopine synthase (ocs), or mannopine synthase (mas) may also be used. Of particular interest are promoters which provide for a high level of expression in plant cells in culture. In particular, 35S or double 35S promoters are desirable in this regard, as well as enhanced promoters, such as an enhanced mas promoter termed MAC (Comai et al., (1990) *Plant Mol. Biol.* 15:373–381). Where the ALDH gene marker is a plant gene, the 5' and 3' regulatory regions naturally associated with the ALDH gene may also find use in the transformation methods described herein.

A transcription termination region may be derived from the 3'- region of the gene from which the initiation region was obtained or from a different gene, or may be provided in the 3' non-coding region of the ALDH gene. Various 3' transcription termination regions which function in plant cells are known to those skilled in the art and may be used in the constructs for ALDH gene expression.

In general, the plant transformation methods of this invention will utilize vectors containing ALDH gene sequences linked to one or more constructs for expression of additional desired gene sequences in transgenic plant cells. In this manner, presence of the ALDH gene acts as a marker to indicate presence of the non-selectable gene constructs. Non-selectable constructs, for example, would include constructs for expression of a desired gene sequence only in particular plant tissues, such as fruit or seed tissues, or constructs for expression of a gene sequence which does not impart a readily detectable phenotype to the transformed plant cells. It is noted, however, that the methods of this invention will also find use where the goal is to provide for transgenic plants expressing an ALDH gene, in which case the transformation vectors will not necessarily contain additional plant expression constructs.

The manner in which the ALDH constructs are introduced into the plant host cell is not critical to this invention, so long as expression of the ALDH gene may be detected by plant cell cultivation and selection on a toxic aldehyde substrate of the gene. For example, Agrobacterium-mediated transformation may be used where the target plant species is capable of being transformed and regenerated by such methods. For example, transgenic plants of many dicot crop plant species may be obtained using Agrobacterium-mediated transformation, whereas most monocot are not amenable to such methods. Binary vectors, such as described by McBride and Summerfelt (*Plant Mol. Biol.* (1990) 14:269–276), find particular use where Agrobacterium is used for plant transformation. With Agrobacterium-mediated transformation, target plant tissues, such as leaf discs, cotyledons, hypocotyl tissues or the like are co-cultivated with Agrobacterium cells containing the ALDH constructs so that the ALDH gene constructs are introduced into the plant cell genome. Direct DNA transfer techniques, such as electroporation, microinjection or DNA bombardment may also be useful, particularly in plant species known to be recalcitrant to transformation by Agrobacterium.

Once the ALDH gene constructs of the instant invention have been introduced into the target plant cells, the cells are cultured on a regeneration medium containing inhibitory levels of the aldehyde target of the inserted ALDH gene, such that cells in which the ALDH gene is expressed may be selected from those in which the ALDH gene is not present. The particular plant cell culture medium will vary depending on the target plant species. Various media useful in plant cell culture methods are well known in the art, and may be optimized for particular plant species. The toxic effects in non-transformed cells may be evidenced by one or more indications of impaired plant cell growth, such as bleaching or senescence of plant tissue. In addition, such selection will differentiate plant cells which contain the ALDH gene, but where the expression level is insufficient to overcome the toxic effects of the aldehyde selective agent.

The cultured plant cells are maintained with regular media transfers and ultimately will form shoots on the regeneration media. The shoots are then transferred to rooting media containing the selective agent and further cultured until roots are formed. Rooting regenerated shoots on the aldehyde selective agent provides an additional selective step for identification of transformed plant cells. Roots which develop from ALDH transformed tissues are longer (as much as 10 fold) than roots which form from non-transformed plant tissues.

The present invention is exemplified by the use of a betaine aldehyde dehydrogenase (BADH) gene as a selectable marker and betaine aldehyde as the selective agent. The substrate specificity of BADH, unlike other related ALDHs is high; BADH metabolizes betaine aldehyde and has little or no activity on other aldehydes, such as acetaldehyde, formaldehyde or proprionaldehyde.

BADH will find use as a convenient selectable marker in many crop plant species, including tomato, tobacco, potato, soybean, rice, cotton and brassicas, such as *Brassica napus* or *B. rapa*. As demonstrated for tomato and tobacco in the following examples, BADH levels of from approximately 2–6 mM, may be used as selective agents in these species. The levels of betaine aldehyde to be used in transformation of a particular plant species may vary depending on the species, but is easily determined using methods known to those skilled in the art, such as the "kill curve" described in the following examples.

BADH genes for use as selectable markers are available from plant species which accumulate the osmoprotectant glycine betaine. Glycine betaine accumulates in the chloroplasts of these plant species as the result of the following pathway:

$$\text{CHOLINE} \xrightarrow{\text{(CMO)}}$$

$$\text{BETAINE ALDEHYDE} \xrightarrow{\text{(BADH)}} \text{GLYCINE BETAINE}$$

The first step is catalyzed by the enzyme choline monooxygenase, and the second step by betaine dehydrogenase (BADH). Glycine betaine accumulation, however, occurs in only a few crop plant species, with sugar beet, barley, and spinach being the major exceptions. As these plants contain an efficient pathway for detoxification of betaine aldehyde, application of the methods of the instant invention to such plant species may require selection at higher levels of betaine aldehyde, for example if a plant cell's native BADH gene is expressed under the plant cell culture conditions used for transformation. The selection efficiency on betaine aldehyde can be increased by increasing promoter strength of the BADH expression construct, for example by using strong plant promoters such as the CaMV 35S or double 35S, or enhanced promoters, such as MAC (Comai et al., supra).

BADH genes have been cloned from spinach, sugar beet and *E. coli*. A high degree of sequence identity is present between plant BADH gene sequences, and related genes from other plant species, particularly those which accumulate glycine betaine, may be obtained by DNA hybridization methods, such as by PCR or library screening, using the known plant BADH gene sequences.

Plant BADH genes are nuclear encoded, but the proteins are transported to the chloroplasts for accumulation of glycine betaine. The chloroplast targeting mechanism for these proteins has not been clearly established. Protein purification and sequence analysis indicates the presence of an 8 amino acid transit peptide, which is atypically short compared to other known transit peptides. For detoxification of betaine aldehyde provided in plant cell culture media, production of BADH in the cytoplasm of transgenic plant cells may provide for higher selection efficiency. The cytoplasm of cells in direct contact with media containing betaine aldehyde likely accumulate high levels of betaine aldehyde in the cytoplasm, and hence, metabolism of the betaine aldehyde into glycine betaine via the action of BADH, would effectively remove the betaine aldehyde from the cell. There are several approaches that could be used to provide for localization of the BADH protein in the cytoplasm. For example, a BADH gene from an organism which does not require plastid targeting mechanisms could be used, such as BADH from *E. coli* or yeast. Where plant BADH genes are used, a construct in which the BADH transit peptide region is remove can be prepared. Alternatively, one could use a translational fusion construct between the BADH cDNA and a protein or peptide fragment that destroys chloroplast targeting and encodes a functional BADH protein.

The invention now being generally described, it will be more readily understood by reference to the following examples which are included for purposes of illustration only and are not intended to limit the present invention.

EXAMPLES

Example 1 Phytotoxicity of Betaine Aldehyde

To determine whether betaine aldehyde (BA) is sufficiently phytotoxic to tomato cotyledon explants to act as a selection agent, and to determine appropriate concentrations for use in the transformation and selection process, a BA "kill curve" is conducted. Sterile seeds from tomato cv. CR3 are germinated on MSSV media (MS salts, 3% sucrose, Nitsch vitamins, 0.8% Bactoagar, pH 6.0), and newly opened cotyledons are excised and placed on regeneration 2Z media (MS salts, 2% sucrose, 2 mg/L zeatin, 0.1 mg/L inositol, Nitsch vitamins, 0.5% Agargel, pH 6.0) containing 0, 2 mM, 5 mM, 10 mM or 20 mM betaine aldehyde (Sigma). BA stock solutions are prepared by dissolving BA at 50 mg/ml in sterile water and filter sterilizing solution using a 0.2 micron filter. The sterile stock solutions are added to media at 55° C.

Cotyledons are assessed for survival and callus production at 10 days and at 5 weeks. The data are summarized in Table 1.

TABLE 1

| Treatment | 10 Days | 5 Weeks |
|---|---|---|
| Control | Green healthy tissue | 20 fully developed calli |
| 2 mM BA | Green tissue; some callus forming | 50 fully developed calli |
| 5 mM BA | Tissue showing some bleaching and some green areas | 50 calli developed; no dead tissue |
| 10 mM BA | Tissue bleaching and dying | all tissue dead |
| 20 mM BA | Tissue bleaching and dying | all tissue dead |

It is evident from the data in Table 1 that betaine aldehyde is phytotoxic in a concentration-dependent manner. Based on these data, selection on betaine aldehyde will provide sufficient toxicity to allow for selection of transformed cells expressing a BADH gene.

Example 2 BADH Constructs

A. Expression Construct Using Mas Promoter

Plasmid pBADH8 (a gift from Dr. Andrew Hanson) contains the approximately 1.8 kb cDNA of spinach the BADH gene (Rathinasabapathi et al. (1994) *Planta* 193:155–162; Weretilnyk and Hanson (1990) *PNAS* 87:2745–2749) as an EcoRI/HindIII fragment in a pBluescript (Stratagene; La Jolla, Calif.) cloning vector.

pBADH8 was digested with PstI which cuts outside of the BADH cDNA, in the polylinker of pBluescript. The linearized plasmid was treated with the Klenow fragment of DNA Polymerase I to blunt the overhanging ends. The plasmid was then religated using a blunt-end ligation reaction (5 Prime-3 Prime Inc.), and the resulting clone was designated pCGN4602. pCGN4602 was then digested with XhoI, which cuts outside of the BADH cDNA, in the polylinker of pBluescript, and the linear plasmid treated with the Klenow fragment of DNA Polymerase I in the presence of dideoxy nucleotide triphosphates (dATP, dTTP, dGTP and dCTP), to fill in the overhangs and create blunt ends. The digested plasmid was then ligated using a blunt-end ligation reaction (5 Prime-3 Prime Inc.). The resulting plasmid, pCGN4603, contained no PstI or XhoI sites.

For expression of BADH under the control of the plant functional mannopine synthase (Mas) promoter, the BADE cDNA was inserted into the Mas expression cassette, pCGN1047, which contains the Mas promoter and Mas terminator and a polylinker region separating the Mas promoter and terminator regions (Comai et al., (1990) *Plant Mol. Biol.* 15:373–381). pCGN4603 was digested with BamHI and Asp718 to excise the 1.8 kb BADH cDNA. pCGN1047 was also digested with BamHI and Asp718, which cut within the polylinker region. The pCGN4604 fragment containing the BADH cDNA was then ligated into the pCGN1047 Mas cassette, such that the Mas promoter would drive the forward (sense) expression of the BADH gene. The resulting plasmid was termed pCGN4604.

B. Linking of BADH Selectable Marker to Antisense PG Construct pCGN4604 was digested with XhoI to excise the entire 3.2 kb Mas:BADH:Mas construct. The 3.2 kb Mas/BADH fragment was ligated into s SalI digested d35S antisense PG construct, pCGN1433 (described below), resulting in pCGN4605. SalI linearizes pCGN1433 and cuts in a region outside of the antisense PG expression cassette. pCGN1433 is an antisense PG construct, where the transcription of antisense PG RNA is under the regulatory control of a CaMV double 35S promoter and an Agrobacterium tml 3' region. The promoter contains nucleotides 6493–7342, 7069–7434 of the CaMV genome (sequence numbering according to Gardner et al. (1981) *Nucl. Acids Res.* 9:2871–2888). The tml 3' region contains nucleotides 6213–7358 of Agrobacterium T-DNA (sequence numbering according to Barker et al. (1983) *Plant Mol. Biol.* 2:335–350).

C. Insertion into Binary Vector

For plant transformation, pCGN4605 was inserted into the *Agrobacterium tumefaciens* binary vector, pCGN1548 (McBride and Summerfelt (1990) *Plant Mol. Biol.* 14:269–276) as follows. pCGN4605 was digested with PstI, and the 7.2 kb fragment containing the Mas BADH::d35S antisense PG expression cassette was ligated into PstI digested pCGN1548, a binary vector containing the Mas-nptII selectable marker, resulting in pCGN4606. In pCGN4606, all three gene constructs, Mas-BADH, d35S-antisense PG and Mas-Kan, are oriented in the same direction relative to the tDNA borders.

Example 3 Tomato Transformation and Regeneration on Betaine Aldehyde

The plasmid pCGN4606 was transformed into *Agrobacterium tumefaciens* strain LBA4404 (also known as 2760). Single colonies containing pCGN4606 were selected for tomato transformation experiments. Sterile cotyledon tissue was obtained from tomato inbred line CR3 seed, and cocultivation performed as previously described (Fillatti et al. (1987) *Bio/Technology* 5:726–730) with the following changes. Following the 48 hour incubation period on the feeder plates, cocultivated cotyledon segments (explants) were transferred onto regeneration medium (2Z media with 500 mg/L carbenicillin) containing betaine adlehyde (Gemini Products) at 400 mg/L (approximately 2.9 mM) and 500 mg/L (approximately 3.6 mM) or 150 mg/L kanamycin (to select for the co-transformed nptII gene conferring resistance to kanamycin). Shoots began to develop in 8 to 12 weeks, and were harvested at 3 week intervals.

Shoots selected on kanamycin were placed on rooting media (MSSV containing 50 mg/L carbenicillin and 50–200 mg/L kanamycin). Shoots selected on betaine aldehyde were transferred to the same rooting media without kanamycin. Roots typically formed within 10–12 days, and the resulting plantlets were screened by PCR for presence of the BADH gene.

Example 4 PCR Screening for Transformation Efficiency

Regenerated tissues were analyzed for the presence of tDNA containing the BADH gene to assess transformation efficiency. Presence or absence of the gene was assessed by polymerase chain reaction (PCR). DNA for PCR reactions was extracted from leaf pieces taken from the developing shoots as follows. Leaves were frozen in liquid nitrogen, and ground in 10% to 20% wt/vol extraction buffer (0.5M sorbitol, 0.1M Tris base, 5 mM EDTA, 3.8 g/L sodium bisulfite, pH 7.5) in eppendorf tubes. Tubes were spun in a microfuge at approximately 10,000 rpm for 5 min. The pellets were resuspended in 200 μL extraction buffer, and 200 μL lysis buffer and 80 μL 5% sarcosyl were added. Tubes were incubated at 65° C. for 15 to 30 minutes, following which 750 uL of chloroform:isoamyl alcohol (24:1) was added, and the samples mixed with a vortex. The samples were then spun at 10,000 rpm in a microfuge for 5 minutes to separate the phases. The aqueous phase was transferred to a clean tube and precipitated with an equal volume of cold isopropanol. Genomic DNA was recovered by centrifugation at 10,000 rpm for 5 minutes. The pelleted DNA was resuspended in 200 μL 1X TE, and incubated for 15 minutes with 0.2 μg/L RNAse A. DNA was precipitated with 600 μL 100 ethanol and recovered following centrifugation. DNA was resuspended in 100 μL 1X TE.

PCR amplification of the BADH gene sequence was conducted as follows. Oligomer primers, BADH F4 (SEQ ID NO: 1) 5' TGATAAGCTTGTAAAATGGA 3' and BADH R10 (SEQ ID NO: 2) 5' GTTACAATGGTGGGTTCAAT 3' were designed to amplify a 210 bp region of the spinach BADH cDNA. The PCR reactions contained 20 μL of genomic DNA, in the presence of 10 mM Tris-HCl, pH 8.3, 50 mM KCl, 2.5 mM $MgCl_2$, 0.05% Nonidet P-40, 1 mM dNTPs (Pharmacia), 1 mM each of the BADH F4 and R10 primers, and 2.5 units of Taq Polymerase (Perkin Elmer Cetus). A cycle regime of 94° C. 15 sec, 55° C. 60 sec, 72° C. 90 sec was repeated 40 times, followed by a 72° C. incubation for 7 minutes. Products of the reaction were visualized following electrophoresis through ethidium bromide infused agarose gels, with the BADH gene product appearing as a 210 bp band. Shoots were scored as either plus or minus for the BADH gene, and the data summarized in Table 2.

TABLE 2

| Selection Media | # Explants | # Shoots | # Rooted | # PCR Positive | Transformation Efficiency /Explants | /Shoots |
| --- | --- | --- | --- | --- | --- | --- |
| Kanamycin | 120 | 36* | 11 | 6 | 5.0 | 16.7 |
| Betaine Aldehyde | 150 | 46** | NA*** | 5 | 3.3 | 10.9 |

*Rooted on 150 mg/l kanamycin
**Pooled data from selection on 400 and 500 mg/L BA
***Rooted without selection The above data indicate that expression of BADH and selection on betaine aldehyde provides a useful selectable marker system for plant transformation.

Example 5 Rooting Selection on Betaine Aldehyde

A. Tobacco

Effective levels of betaine aldehyde for rooting selection as a screen to identify transformed plantlets were determined. Wildtype tobacco plants (cv. Wisconsin 38) and tobacco plants (cv. Wisconsin 38) with the BADH 4 gene (Rathinasabapathi et al. (1994) *Planta* 193:155–162) were placed on MS 1/0/.15 with levels of betaine aldehyde ranging from 0 mM, 2 mM, 4 mM, 6 mM, 8 mM. (BADH 4 contains an EcoRI/BamHI fragment of a sugar beet BADH clone under the regulatory control of a CaMV 35S promoter.) Betaine aldehyde is purchased from Gemini Bioproducts. MS 1/0/.15 is 34.57 g/l Murashige and Skoog minimal organics 1118, 1 mg/l IAA, 0.15 mg/l kinetin, pH 5.55, 0.7% bactoagar. Media is autoclaved for 20 minutes at 121° C., and sterile betaine aldehyde is added when media has cooled to 55° C. Meristems from tobacco plants were subcultured on the media. The number of samples tested was 10 plants per treatment, with the following exceptions: transgenic tobacco at 2 mM treatment—8 plants; wildtype tobacco at 0 mM treatment—6 plants; wildtype tobacco at 6 mM treatment—11 plants. After two weeks on media, plants were scored for rooting. Data indicating the presence or absence of roots are provided in Table 3.

TABLE 3

| Betaine Aledhyde Concentration (mM) | % Wildtype Rooted | % BADH 4 Rooted |
|---|---|---|
| 0 | 100A | 100% |
| 2 | 10 | 87.5 |
| 4 | 30 | 80 |
| 6 | 9 | 40 |
| 8 | 10 | 10 |

In addition to scoring for the presence or absence of roots, properties of the roots were noted for plants scored as positives. Roots which developed from meristems from wildtype plants were approximately 2–4 mm long. Roots which developed from meristems from transgenic BADH expressing plants were 2–3 cm long at the 2 mM betaine aldehyde and 4 mM betaine aldehyde level. In addition, plants at 0 mM betaine aldehyde were slightly taller than plants at any of the tested betaine aldehyde levels. These data indicate a clear correlation in betaine aldehyde level and inhibition of rooting, and demonstrate that rooting on betaine aldehyde provides a useful screening method for evaluating plantlets resulting from transformation and regeneration on betaine aldehyde.

B. Tomato

Tomato cotyledon segments are transformed and regenerated as described in Example 3 with the CaMV 35S BADH 4 construct described above. The resulting shoots are transferred to rooting media (MSSV plus 50 mg/L carbenicillin) containing 400–700 mg/L betaine aldehyde. After culture for approximately one to two weeks on the betaine aldehyde rooting media, the plantlets are evaluated to select positive transformants. Plantlets developing elongated roots are selected as positive for expression of the BADH gene, and can be distinguished from non-transformants which have stunted roots. Plantlets selected as positives are transplanted into soil and grown to produce transformed plants.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of plant cell transformation, wherein said method comprises:

introducing into cells of a plant species sensitive to growth inhibition by a phytotoxic aldehyde, a DNA construct comprising as operably linked components, a promoter functional in said plant cells, a DNA sequence encoding an aldehyde dehydrogenase capable of detoxifying said phytotoxic aldehyde, and a transcription termination region functional in said plant cells, culturing said plant cells in a plant growth medium comprising said phytotoxic aldehyde, and selecting transformed plant cells demonstrating resistance to said phytotoxic aldehyde.

2. A method according to claim 1, wherein said method further comprises regenerating a transformed plant from said transformed plant cells.

3. A method according to claim 1 wherein said phytotoxic aldehyde is betaine aldehyde.

4. A method according to claim 3 wherein said DNA sequence encodes betaine aldehyde dehydrogenase.

5. A method according to claim 4 wherein said DNA sequence is from sugar beet or spinach.

6. A method according to claim 4 wherein said DNA sequence is from E. coli.

7. A method according to claim 1 wherein said DNA construct is introduced into said plant cells by cocultivation with Agrobacterium.

8. A method according to claim 1 wherein said DNA construct is introduced into said plant cells by bombardment.

9. A method according to claim 1 wherein said plant species is a crop plant species.

10. A method according to claim 1 wherein said crop plant is selected from the group consisting of tomato, potato, rice, brassica, cotton and soybean.

11. A method according to claim 1 wherein said promoter is a CaMV 35S promoter.

12. A method of plant cell transformation, wherein said method comprises:

introducing into cells of a plant species sensitive to growth inhibition by betaine aldehyde, a DNA construct comprising as operably linked components, a promoter functional in said plant cells, a DNA sequence encoding a betaine aldehyde dehydrogenase capable of detoxifying said betaine aldehyde, and a transcription termination region functional in said plant cells, culturing said plant cells in a plant growth medium comprising said betaine aldehyde, and selecting transformed plant cells demonstrating resistance to said betaine aldehyde.

13. A method according to claim 12, wherein said method further comprises regenerating a transformed plant from said transformed plant cells.

14. A method according to claim 12, wherein said DNA sequence is from sugar beet or spinach.

15. A method according to claim 12, wherein said DNA sequence is from E. coli.

16. A method according to claim 12, wherein said DNA construct is introduced into plant cells by co-cultivation when Agrobacterium.

17. A method according to claim 12, wherein said DNA construct is introduced into said plant cells by bombardment.

18. A method according to claim 12, wherein said plant species is a crop plant species.

19. A method according to claim 12, wherein said crop plant is selected from the group consisting of tomato, potato, rice, brassica, cotton and soybean.

20. A method according to claim 12, wherein said promoter is a CaMV35S promoter.

21. A method of plant cell transformation, wherein said method comprises:

introducing into cells of a plant species sensitive to growth inhibition by a phytotoxic aldehyde selected from the group consisting of acetaldehyde, formaldehyde, proprionaldehyde, butyraldehyde, and betaine aldehyde, a DNA construct comprising as operably linked components, a promoter functional in said plant cells, a DNA sequence encoding an aldehyde dehydrogenase capable of detoxifying said phytotoxic aldehyde and a transcription termination region functional in said plant cells, culturing said plant cells in a plant growth medium comprising said phytotoxic aldehyde, and selecting transformed plant cells demonstrating resistance to said phytotoxic aldehyde.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic oligonucleotide ( x i ) SEQUENCE DESCRIPTION: SEQ ID NO:1:

TGATAAGCTT GTAAAATGGA                                         2 0

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE:Other nucleic acid
        ( A ) DESCRIPTION: Synthetic oligonucleotide ( x i ) SEQUENCE DESCRIPTION: SEQ ID NO:2:

GTTACAATGG TGGGTTCAAT                                         2 0